United States Patent [19]

Spies

[11] Patent Number: 5,193,883
[45] Date of Patent: Mar. 16, 1993

[54] PROCESS FOR CONTROLLING LONGWALL SHEARING AND HEADING MACHINES ALONG A CUTTING HORIZON BETWEEN COAL AND ROCK

[76] Inventor: Klaus Spies, Frennetstr. 49, 5100 Aachen, Fed. Rep. of Germany

[21] Appl. No.: 688,501
[22] PCT Filed: Sep. 19, 1990
[86] PCT No.: PCT/EP90/01587
§ 371 Date: Jul. 15, 1991
§ 102(e) Date: Jul. 15, 1991
[87] PCT Pub. No.: WO91/04392
PCT Pub. Date: Apr. 4, 1991

[30] Foreign Application Priority Data

Sep. 25, 1989 [DE] Fed. Rep. of Germany ....... 3931915
Aug. 11, 1990 [DE] Fed. Rep. of Germany ....... 4025551

[51] Int. Cl.[5] .................. E21B 49/08; E21C 39/00; G01N 1/04
[52] U.S. Cl. .................. 299/1.1; 73/864.41; 299/45
[58] Field of Search .......... 299/1.05, 1.1, 1.2, 299/1.6, 45; 175/50; 73/864.41

[56] References Cited

U.S. PATENT DOCUMENTS 4,332,301 6/1982 Jonell .................. 73/864.41 X
4,502,951 3/1985 Koenig et al. .......... 73/864.41 X

FOREIGN PATENT DOCUMENTS 01837 9/1980 PCT Int'l Appl. .
2190939 12/1987 United Kingdom .

Primary Examiner—David J. Bagnell
Attorney, Agent, or Firm—Price, Heneveld, Cooper, DeWitt & Litton

[57] ABSTRACT

Process and device for controlling longwall shearing and heading machines along a cut horizon between coal and rock. The horizon is produced by a cutting tool arrangement attached to the machine and followed by a sensor which distinguishes between coal and rock. The values measured by the sensor are converted to control impulses which guide the cutting tool in the cut horizon. Mineral samples are taken, continuously or at short distances apart, behind the cutting tool arrangement, and the sample material is analyzed in the sensor. The result of the analysis is compared with a standard value and the deviation from the theoretical value is used as the value of the control impulses.

26 Claims, 11 Drawing Sheets

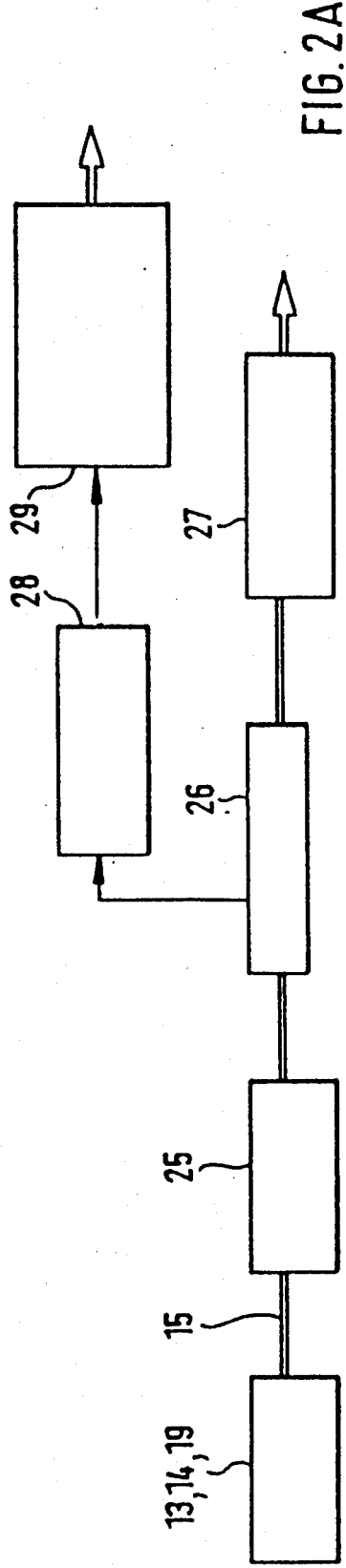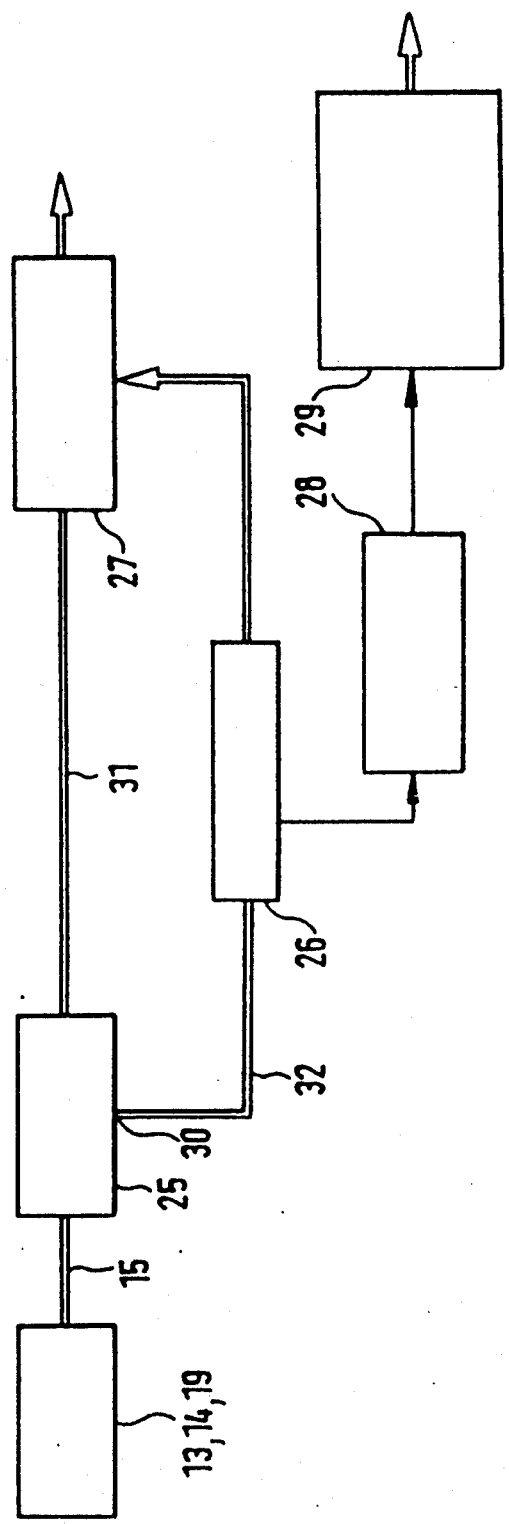

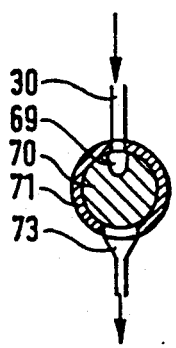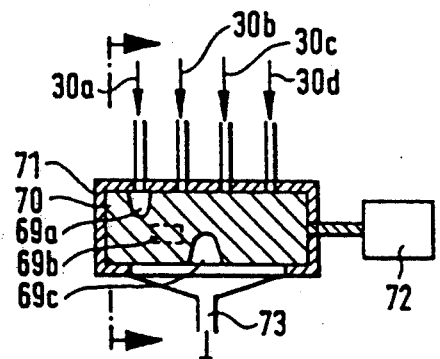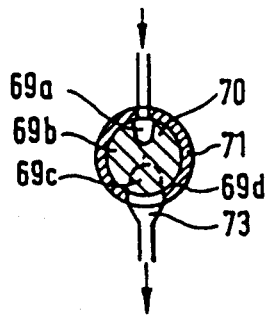
FIG 8B  FIG 8C  FIG 8D
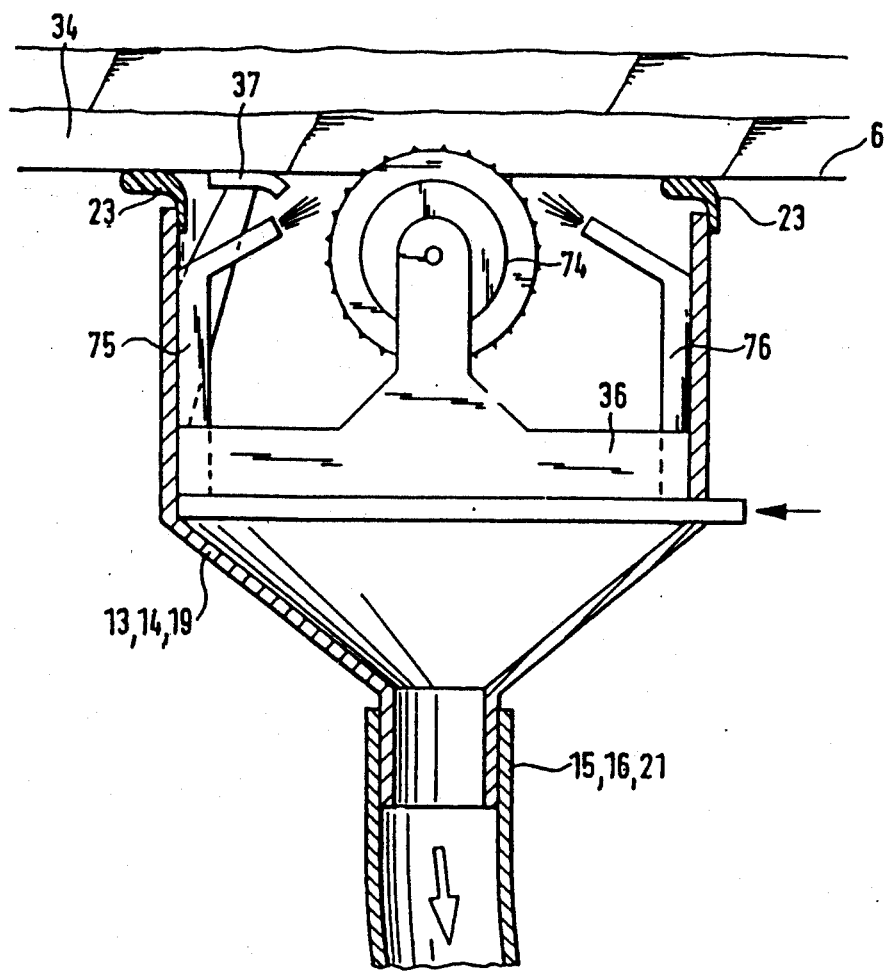
FIG. 9

PROCESS FOR CONTROLLING LONGWALL SHEARING AND HEADING MACHINES ALONG A CUTTING HORIZON BETWEEN COAL AND ROCK

This invention deals with a control procedure for extraction plants and propulsion machines along a crevasse between coal and rock. More particularly, this invention relates to controlling reaming and advance machines along a cutting horizon between coal and rock, based on a cutting tool configuration affixed to a machine, fitted with a sensor able to differentiate between coal and rock areas, whose measuring values are transformed into actuating impulses, which guide the cutting tools to the cutting horizon. The invention also deals with a unit capable of executing this procedure. The invention relates specifically to the automation of coal extraction, preferably by using cutting machines, mainly roller loaders and continuous miners, but also extraction machines which process in ploughing motion as, for instance coal planes.

Depending on the design and format of the cutting tool layout in machines of this type, the unit can be directed to the cutting line between the coal lode and the rock with a control unit, and assume the desired position. The invention deals specifically with the control of those machines which enable automation of coal extraction from irregular or often geologically faulted lodes, whereby a sensor of robust material, and specifically designed to withstand conditions in underground mining, enables selection between coal lodes and adjacent rocks, obtaining control parameters enabling adjustments to be made to the tooling, so that the unit is automatically and speedily returned to the desired position.

The invention is based on a known technique. This has been implemented behind the cutters or tool retainer of a cutting extraction machine as a sensor, to ascertain whether the cutting line is within the coal lode or in the rock. The known technique uses radio-active isotopes as sensors; these have a short period of decay and a Geiger counter, which measures beams reflected between sender and receiver. The result depends on whether the dispersed rays penetrate coal or rock areas. It was however discovered that, due to the multitude of external influences on the intensity of reflected beams registered by the receiver, it was not possible to separate the typical coal and rock characteristics, since the static interference is much stronger than the differences in signals emitted from the coal or rock lodes.

Subsequent research has, with a few exceptions, concentrated on a combination of 4 sensors operating according to different physical methods, to compensate for inherent disadvantages and inexact measurements obtained from the various mechanisms by the 4-fold sensoring combination. However, the results obtained are not completely reliable. This applies specifically to the measuring chisel, radioactive beams, and a combination of visible and infrared light or sapphire laser beams. Measuring chisels used to capture the cutting force and transferring the results to the analysis unit also do not give exact information of whether the cut is made in coal or in neighbouring rock areas. Some lodes or some parts of a lode have areas in which the coal is a great deal harder than the adjacent rock formation. For instance, when analysing an adjacent area which is a combination of earth and root matter, the attempt at selection can in fact produce a false finding, resulting in incorrect control impulses which place the cutters or cutting units into the softer mineral, e.g. into the adjacent rock and ingrowth area.

In common with the known equipment or procedures for controlling extraction plants and propulsion machines along a crevasse between coal lodes and rock face, the invention also uses methods and laws known in physics, which however may differ in details, for simple direct and immediate selection between coal and rock lodes, thus enabling reliable control of the cutting equipment. This function is resolved by controlling reaming and advance machines along a cutting horizon between coal and rock, based on a cutting tool configuration affixed to a machine, fitted with a sensor able to differentiate between coal and rock areas, whose measuring values are transformed into actuating impulses, which guide the cutting tools to the cutting horizon.

According to the procedures used in the invention, suitable mineral samples are taken continuously or in short intervals from the excavation site; these samples are removed from the rock/coal interface. This sampling can be handled by a comparatively simple unit. The minerals taken from the cutting section behind the cutting tools or tool units, being the surface of the remaining mineral contents or the boundary of the mining area, is analyzed with the sensor to ascertain the proportion of coal and rock content in the sample. Analysis and samples are then compared, so that the control system can be adjusted with sufficient speed to react to the cutting equipment responses at the cutting level.

This invention not only enables unique selection between coal lodes and adjacent rocks, it can also detect "intergrowth", e.g. mixed deposits of slate and root matter, which frequently occur at the boundaries between lodes and adjacent rock. This type of ingrowth does not interfere adversely with the automated coal winning procedure resolved by this invention. In addition, the sensor also fulfils another requirement. The cutting level at the rock face can be adjusted from case to case, according to threshold values for shale or coal content, whereby actuating variables are activated at threshold values preset to either above or below the standard. The invention therefore offers the advantage of avoiding cutting into the adjacent rock or into shale containing ingrowths, e.g. into packing at the hanging roof or root matter at base of the seam; this greatly reduces the shale content of the raised and weighed tonnage. On the other hand, no coal residue is left at the hanging roof or at the base of the seam. The total of available coal to be conveyed is not reduced, so that no coal remains to emit gases, thus avoiding the likelihood of causing firedamp.

Since the mineral removed from the mine face is analyzed, it is possible to use analysis procedures which guide the cutting tool set exactily on to the boundaries between lode and adjacent rocks, should this be required. Therefore, this invention creates the prerequisites for automated coal extraction and, in addition, also enhances the extraction procedure specifically inasfar as the currently used mechanized longwall operations are concerned, to make the operations technically more effective, and to greatly improve their cost-effectiveness.

The invention is also capable of obtaining a representative image of the consistency of minerals available immediately behind the cutting level when the mineral samples taken are mixed and crushed prior to being analyzed. This enables the analysis of small samples taken from a relatively large volume stream. The sample size can be reduced several times. The average combination of mineral quantities analyzed then exactly represents the composition of the entire sample.

Immediately a mineral sample is analyzed, another analysis must be prepared and carried out. This requires that the sample material which has been analyzed is disposed of. This procedure may be simplified when the waste material from the mineral samples and the sample material tested are disposed of in continuous mode or in short intervals so the mineral streams are combined prior to their disposal.

If it is intended to ascertain representative values for coal or adjacent rock in the cutting area covering the total width of the level, it is recommended that the sampling procedure covers the entire working width of the cutting tools, and samples are either analyzed singly or in combination. In specific cases, this also offers the option of analyzing samples individually to obtain more precise evaluations of coal and rock content at the cutting level across the entire width.

It is also advisable that the crushed mineral taken from cuts into the cutting horizon is used as sample material. This offers a provision ensuring that samples are taken starting from the cutting area and extending to a defined width and depth. This gives a representative image of the composition of available minerals immediately behind the cutting level. The cuts can be made with mechanical tools, but it is also possible to use pressurized water techniques or separation and detaching procedures.

When the sample material is crushed prior to analysis, the precision of analyses results is increased. Breaking samples into smaller portions leads to blending of the samples and, as a rule, also to a thorough mixing of the sampling material.

The type of analysis applied to the sample material is of major importance for the effectiveness of the invention. Basically, the content of coal and rock can be ascertained in a multitude of ways. The most effective means may be when the sample is heated, and the coal content is defined either by heat measurement or by gas analysis. Here, the reduced samples is either heated until the coal content is burned away, whereby the heat created by burning of the coal content in the minerals is measured. Or, the sample material containing a mixture of coal, rock, and coal and rock mixtures heated up to the point where the coal content starts to carbonate, releasing the gas content. A number of gas analysis and detection devices have previously been created for other applications. These can be used within the frame work of this invention to ascertain exact measured values, which can be transferred as actuating variables.

Another analytical method, namely photometric analysis, enables wet analysis of sample material. This is recommended in situations subject to high firedamp probability during operations, due to the presence of flammable gases.

The implementation formats introduced by the invention work precisely, so that it is not only possible to determine whether the cut was made into coal or rock at cutting levels sited at the boundaries between lode and adjacent rock areas, but also for applications aimed at sorting samples into more or less rock-containing specimens. Specifically in situations where it is intended to cut out only parts with a low rock content from a large lode, the provisions in the invention result in measured values and therefore actuating variables of great precision, thus enabling guiding the cutting tools along boundaries, beyond which the rock content in the coal is unacceptable.

It is advantageous to establish a reference on standard value by selected, empirical sampling. Here the actual measured values are compared with standard values programmed during a single or several training passes by the reaming unit.

If no coal is to remain at the bottom or top of a lode, it is desirable to control the unit in such a manner that the cutting tool traverses closely to the boundary between coal and rock. Then take a sample of the rock area. In this case it is not easy to ascertain the depth of cut into the rock, nor whether the cut was made near the boundary between rock and coal. Therefore, the standard value is based on the analyzed value for rock, and that this value is used to set the cutting tool unit into the coal face in time intervals, whereupon automatic control is resumed. Here, a computer or processor emits a control impulse after a specific distance has been traversed, for example after travelling 3 of 5 meters; this control impulse is used to move the cutting tools in the direction of the coal lode. When a sample taken from the cutting area contains too little coal to make it viable, the cutting boundary has been reached, and automatic control is resumed; now samples are taken a few centimeters into the rock area. These intermediate checks enable placing the cutting tool precisely into the boundary between coal and rock.

Details, characteristics and other advantages inherent in the invention can be found in the following descriptions of devices used for implementing the procedure as described using drawings.

BRIEF DESCRIPTION OF THE DRAWINGS

FIG. 1b is an enlarged, detail view of the upper roller of the, roller loader of FIG. 1a.

FIG. 1c is an alternative, enlarged, detail view of the upper roller of the roller loader of FIG. 1a.

FIG. 2a is a flow chart of a process according to the present invention.

FIG. 2b is a flow chart of an alternative embodiment of a process according to the present invention.

FIG. 8b is a cross-sectional view of the discontinuous dosing unit of FIG. 8a, taken along section line B—B.

FIG. 8c is a cross-sectional detail of an alternative, multiple sample discontinuous dosing unit for the process of FIG. 8a.

FIG. 8d is a cross-sectional view of the dosing unit of FIG. 8c, taken along section line C—C.

FIG. 9 is a longitudinal sectional view of a third embodiment of a sampling unit according to the present invention.

DESCRIPTION OF THE PREFERRED EMBODIMENTS

Figure 1A:
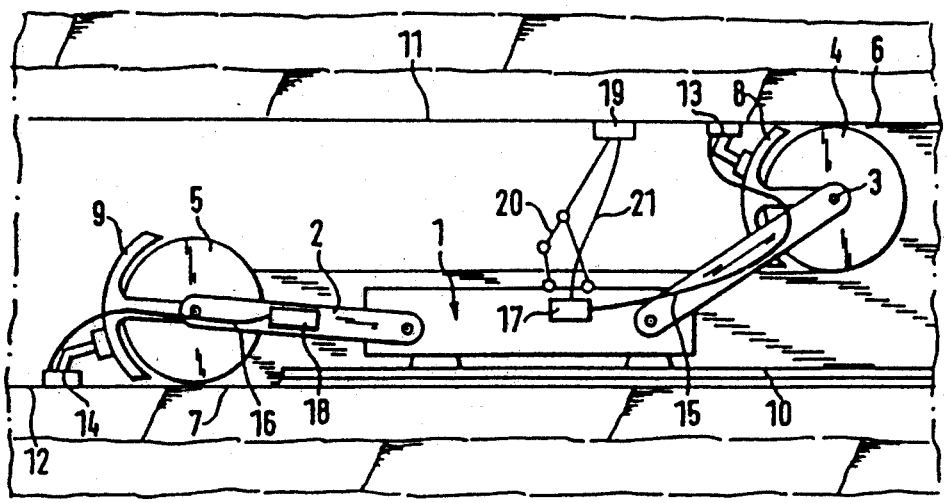
FIG. 1a is a fragmentary, sectional view of a mining operation showing a side elevational view of a roller loader adapted according to the present invention.
Figure 1B:
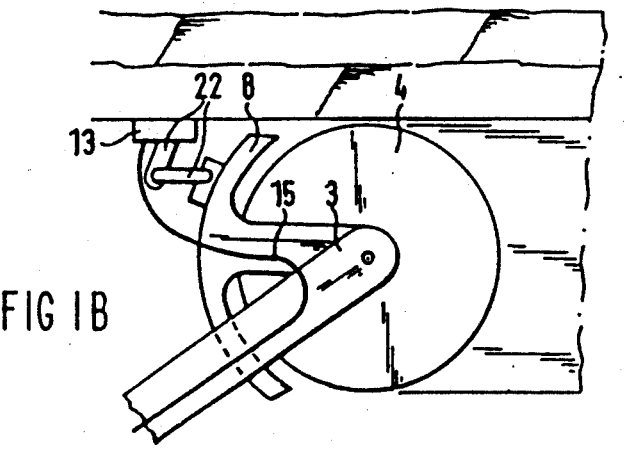
Figure 1C:
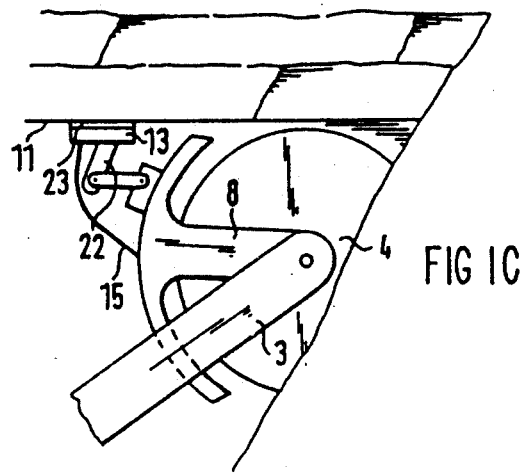

According to FIG. 1a, the roller loader 1 has two mobile lugs 2 and 3 sited at the ends, to which the rollers 4 and 5 are attached to serve as cutting tool units. During active operation, the leading roller 4 is guided along the top wall 6 to ensure that the lagging delay is kept to a minimum, whilst the lagging roller 5 cuts into the base of the seam 7. Mobile loading plates 8 and 9 transport the coal cut free by reamers, which are not displayed, to the chain scraper conveyor 10 on which or beside which the roller loader runs along the longwall.

When automating the reaming procedure or the advance work, the rollers 4 and 5, e.g. the cutting tool units, are lead along the boundaries at the top wall 6 or the base of the seam 7. Since neither boundary is smooth, but is riddled with wavy lines and faults, this ensures that no coal remains and that the adjacent rock is not cut at the same time. Sensors provided to assist in this task are fitted to the reaming or advance machine, so that they can ascertain, immediately behind the cutting tools and their tooling whether the cutting horizons 11 and 12 at the roof or the base of the seam are situated in the coal or in the rock area. For this purpose, the roller loader displayed has a sampler 13 and 14 attached either to or behind each of the reamer plates 8 and 9. There is no drawing of a method devised in the invention which is based on fixing the sampling units 13 and 14 not to the mobile loading plates 8 and 9 but immediately to the machine body or the lugs 3, as freely movable units. Hosepipes 15 and 16 and/or pipes fitted with articulations feed the loose sampling material to the secondary analyzers 17 and 18 or to any other equipment for sample preparation, to the mixing devices and to the measuring or disposal units. These transporters are fitted either to the machine body 1 as shown for analyzer 17, or at a lug 2 as shown for analyzer 18. Conveyor units 15 and 16 are fitted in such a manner as to be sufficiently protected against external damage, specifically against falling rocks and coal.

FIG. 1 a shows, in fine line drawing, another format of affixing the sampling unit 19 to an articulated lever 20 on machine body 1. Hosepipes 21 for transporting the samples taken and fed along the articulations. The drive has a broad adjustment range, e.g can adapt widely to changing lode sizes, is of robust construction in order to withstand falling rocks and coal. According to FIGS. 1a-1c, this is a 4-link unit with sliding and turning pairs 22.

Linkages 22 with lever pairs are used even when the sampling equipment 13 is fitted to the reaming and loading units 8. These move the sampling equipment 13 into the working position with an actuating cylinder when the reaming plate 8 is in the prescribed position. Changes in the position of the reamer 8 during actual operations in comparison to the current position of the lug 3, and changes in the angle of the lug 3 followed by a necessary correction in the reamer plate 8 as soon as the lode depth changes are compensated for by an automatic adjustment of the linkage 22. This ensures that the sampling unit is always in the optimum position. When sampling with a reaming unit with tool retainers which are subject to constant movement during the process, it may be better to forego using detaching tools in favour of simple suction units, which can switch in or open when the tool retainer is in a suitable position near the cutting horizon, e.g. normally when it approaches the adjacent rock.

Figure 1D:
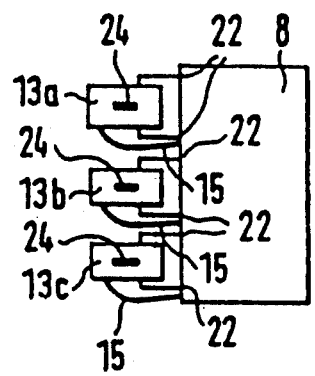
FIG. 1d is a top plan view of the detail of FIG. 1c.
Figure 1E:
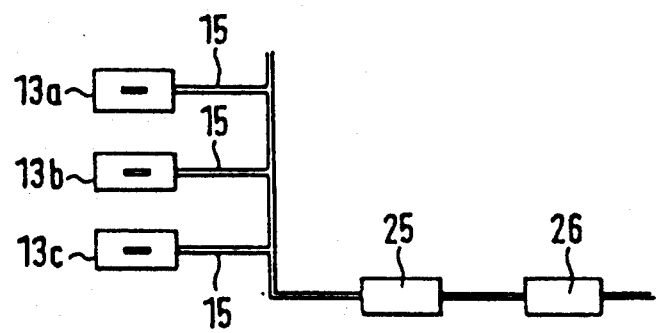
FIG. 1e is a schematic diagram showing one arrangement of the components of FIG. 1d.
Figure 1F:
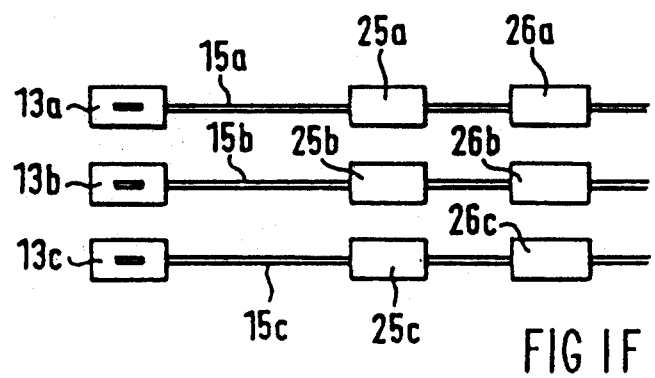
FIG. 1f is a schematic diagram showing an alternative arrangement of the components of FIG. 1d.

When the cutting level demands this, several sampling units are fitted in series behind the cutting unit FIGS. 1d-1f. This enables taking representative samples across the full width of the lode. In accordance with the example illustrated in FIG. 1d, several sampling units 13 are aligned adjacent to each other, affixed with linkages 22 and actuating cylinders (not shown) to reaming or loading plates 8; these are swivelled around the roller loader lug 3 when changing directions.

The sampling units aligned in series 13a, 13b, 13c have fitted sealing sleeves 23 (FIG. 1c) and sample removal chisels 24, and are allocated to cover the entire cutting horizon; they are fitted behind the reamer plate 8 in a position immediately behind the tooling retainer. The mineral extracted is transported in the hosepipes 15 and united to a shared stream (FIG. 1e), which is then transported by the pipes 15 to a sample preparation unit 25 and on to the downstream analyzer 26.

In cases where an exact analysis of the coal and rock content across the total width is required, sample material taken by sampling units 13a to 13c can be fed separately across hosepipes 15a to 15c to several sample preparation units 25a to 25c and to separate analyzers 26a to 26c (FIG. 1f). The results will be three measured values, thus giving a more detailed measurement for the cutting horizon.

According to the example given, the individual system components sampling, sample transfer, sample preparation, analysis, measuring and disposal are chained as displayed in FIGS. 2a and 2b. According to FIG. 2a, the sample material is fed from the sampling units 13, 14, 19 via pipelines 15 to the sample preparation unit 25, then to the analyzer 26 and passed to the waste disposal unit 27, which places the used sampling material in a safe and hygienic format into the longwall area. Measured values obtained by the analyzer are transferred to a converter 28 which, when measured values deviate from standard actuating variables for the control unit 29 of the cutting tool configuration, transfers these values to that unit, so that cutting tools can be adjusted either mechanically, pneumatically or hydraulically. The uniform stream across all modules ensures that measuring is at an even pace, and can be exacted speedily, uniquely and exactly.

Since the invention is not limited to a single analyzer 26 for a specific physical or chemical procedure, it is also possible to process small samples. According to FIG. 2b, only parts of the total stream are fed to the analyzer 26 in continuous or discontinuous mode; the combination of coal and rock content of this stream corresponds exactly to the mix ratio of the total sample. The stream from sampling units 13, 14, 19 is thoroughly mixed in module 25. A partial stream is removed at or near the outlet 30 of this module; this stream is, in relation to the total stream flowing through the transfer units 15, much reduced but still representative of the total compounds transported by stream 15. The main stream flowing from sample preparation unit 25 is fed across connection 31 and disposed of 27, whilst the reduced stream taken from 30 is fed into analyzer 26 for testing. The analyzer is sited in an adjacent arrangement, to ensure that the speed of waste material 15, 31 and speed of the sample material destined for analysis 26 flowing through is the same. Therefore, the analysis can be executed in concert with the sampling, and measured results correspond in sufficient exactness to the coal and rock content within the cutting horizon.

To ensure that the sample based on selected physical and chemical test procedures fed into the analyzer 26, is extremely small in comparison with the volume stream after sampling, it is possible to split the stream again in the connection line 32 between branch line 30 and the analyzer 26.

The sampling units 13, 14, 19 can be used for all physical and technical measures in continuous and discontinuous sampling procedures, e.g. in mechanical or hydraulic sample collection or a combination of these two methods. Hydraulic sample taking, for instance using high pressure water jets, can be combined with transferring the sample by hydraulic means plus a material analysis, which enables defining the content of coal and rock in the water as carrier medium.

Figure 3A:
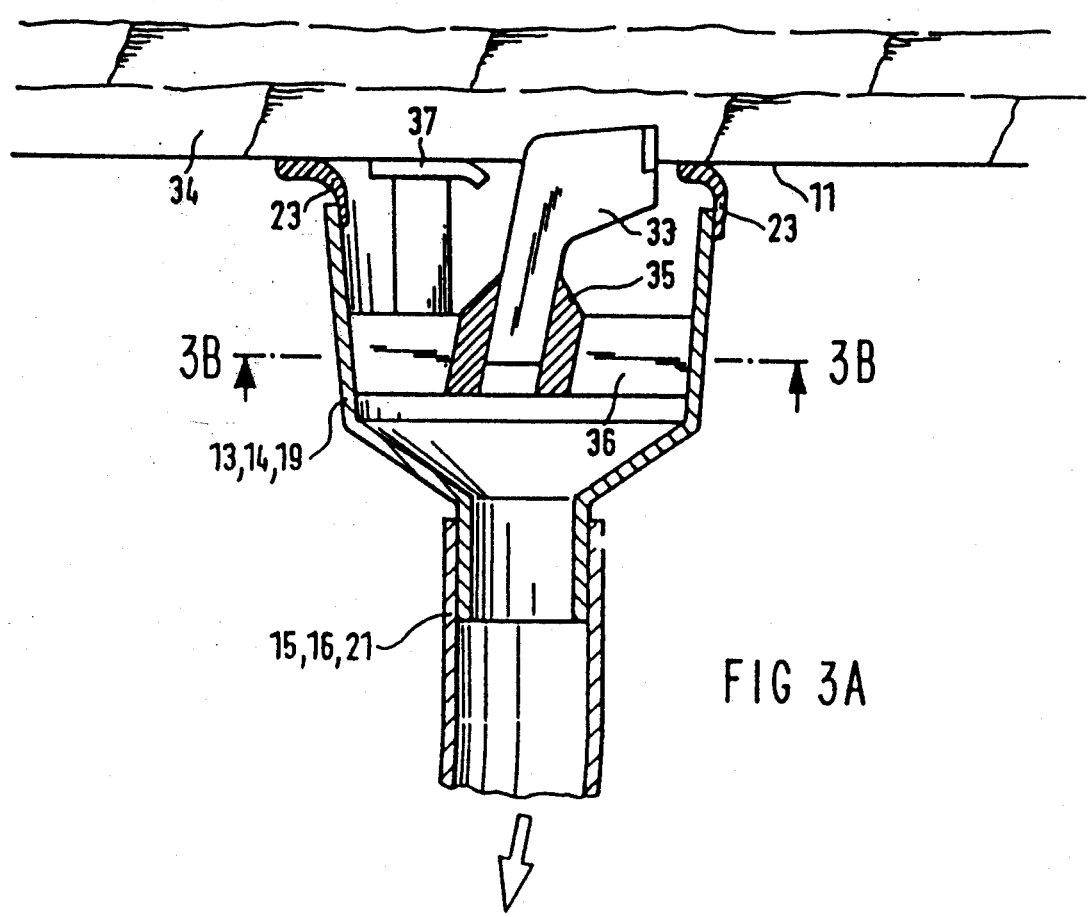
FIG. 3a is a longitudinal sectional view of one embodiment of a sample taking unit according to the present invention.
Figure 3B:
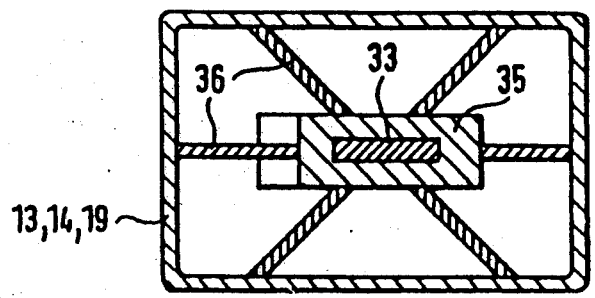
FIG. 3b is a cross-sectional view of the sample taking unit of FIG. 3a, taken along section line A—A.

Sample taking units 13, 14, 19 according to FIGS. 3a and 3b should preferably use a carbide tipped chisel 33 which produces a continuous slit 34 in the cutting horizon 11. The chisel retainer 35 is ribbed 36; the sample material drops down between these ribs, and lands in the transfer line or on the conveyor unit 15, 16, 21. A cutting depth delimiter 37 ensures that the cutting depth allocated for the sampling cut 34 remains steadily at the preset value. Sealing sleeves ensure that no dust or foreign matter can enter from external sources, so that the material can not be contaminated nor be lost. Round shaft chisels or cylindrical chisels may replace the flat chisel 33 displayed.

Figure 4:
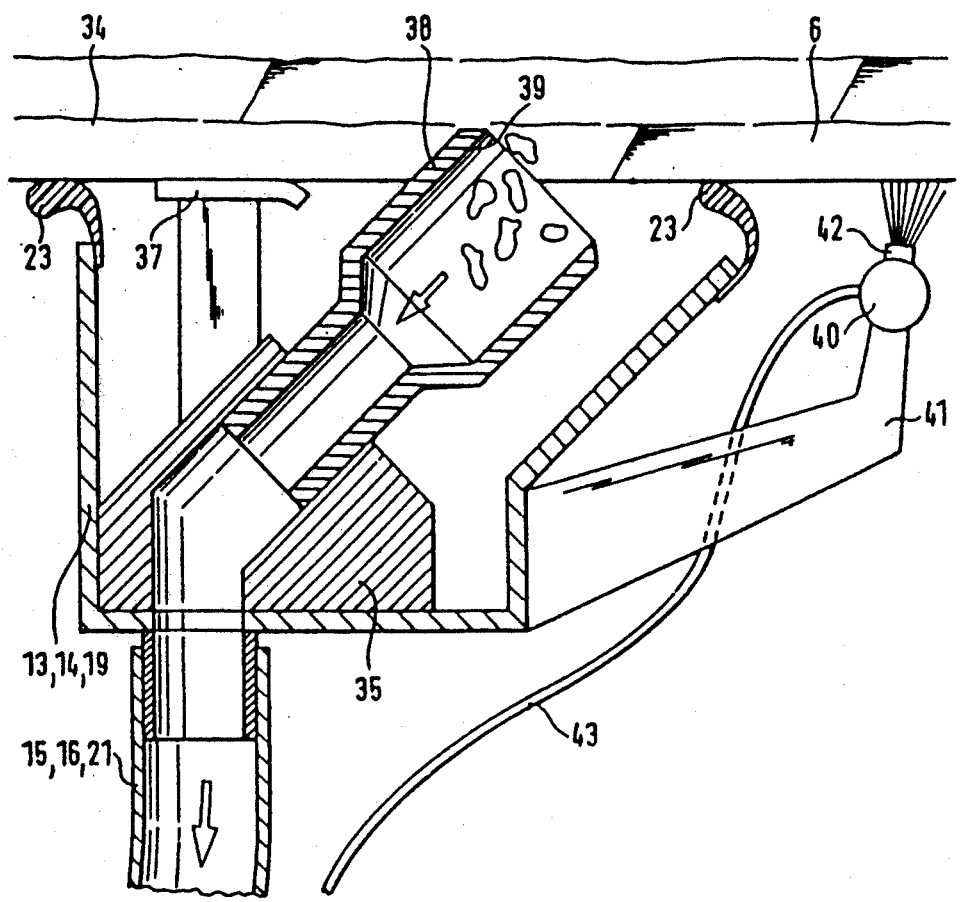
FIG. 4 is a longitudinal sectional view of a second embodiment of a sample taking unit according to the present invention.

The hollow chisel 38 shown in FIG. 4 is most suitable for pneumatic transfer of sampling material. The housing, sealing sleeve 23 and cut depth delimiter 37 are configured as shown in FIGS. 3a and 3b. The chisel 38 however is cylindrical, sharpened at the cutting sides 39, and hollow as is the chisel retainer 35; this enables the loose material to pass through chisel and retainer, and to drop into the transfer units 15, 16, 21.

It is possible to affix a cleaning unit 40 ahead of all concept variants 13, 14, 19 for sample taking. This unit is affixed to the lug 41, has jets 42 inserted, and can be fed with water from the pipeline 43. Apart from the jets, it is also possible to fit brushes, which are not shown in FIG. 4. The cutting area must be scrupulously clean, specifically when taking samples from the cutting area at the bottom of a seam.

Figure 5A:
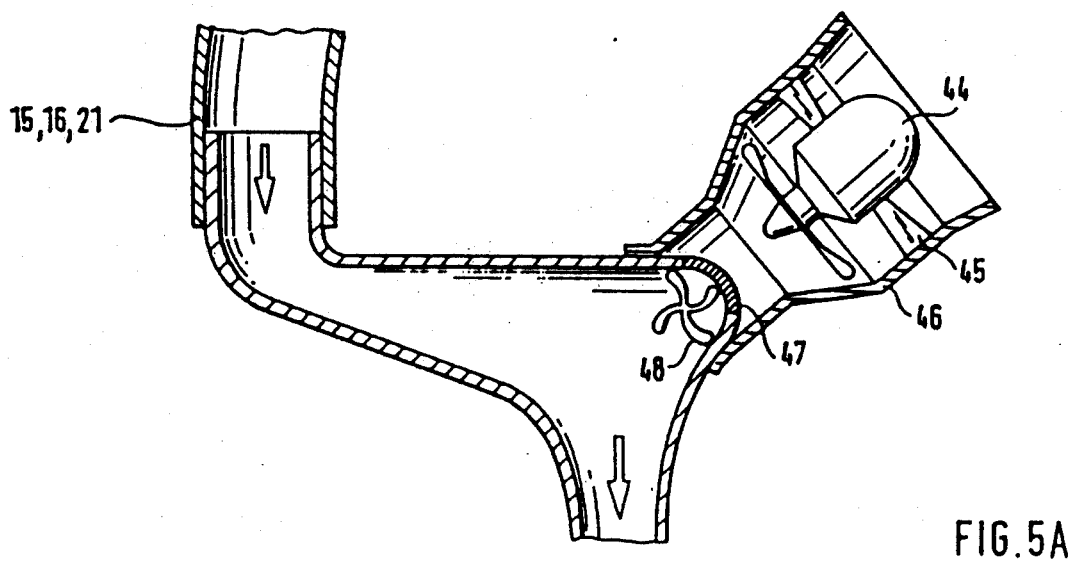
FIG. 5a is a fragmentary, cross-sectional view of a pneumatic sample material transport according to the present invention.
Figure 5B:
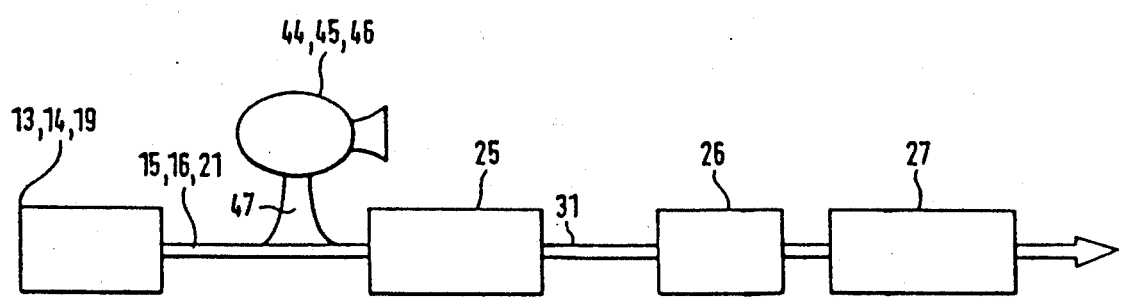
FIG. 5b is a schematic diagram of a process according to the invention using pneumatic sample material transport.

According to FIGS. 5a and 5b, the extracted sample material is transported pneumatically. A blower 44 connected via fins 45 contained in the housing 46 generates overpressure, which is used to transport the sample material from the sample taking units 13, 14, 19 to the sample preparation unit 25. A finely meshed sieve or filter cloth 47 separates the sample material to be conveyed from the air flow; the cleaning unit 48 should preferably be made up of rotating brushes. This will prevent that the sieve or the cloth 47 clogs up after a period of use.

Figure 6:
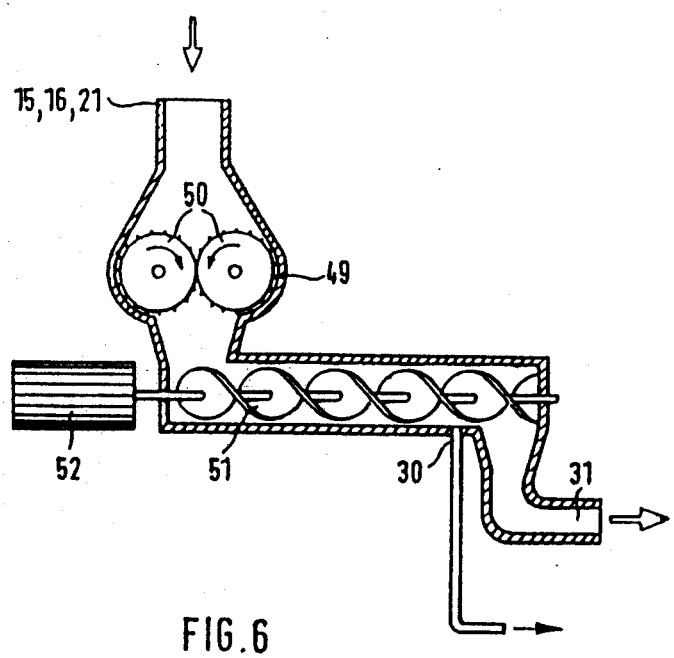
FIG. 6 is a cross-sectional view of a sample preparation crushing device according to the present invention.

According to FIG. 6, the preparation of samples for analysis is dealt with by transferring the material to a crushing or grinding unit 49 between rough-surfaced, high-speed rollers 50 by force of gravity. To achieve a constant consistency of the ground sample material, a high-speed mixing spiral 51 is sited downstream of the crushing unit 49. The high-speed rollers 50 and the high-speed spiral mixer 51 work at absolutely constant revolutions per minute, thus guarantee an absolutely constant flow of the large volume stream. The grinders 50 and the spiral mixer should ideally be driven by synchronous motors, which produce constant rotations independent of loading.

According to FIG. 2b, a small partial stream is taken off at the end of sample preparation 15, 16, 21. This is handled by a dosage unit 30. The waste is then transported in stream format into the waste disposal unit 27. Dosing unit 30 can, for instance, comprise an exactly dimensioned opening or flap, which only permits a strictly defined quantity of the finely ground and thoroughly mixed sample material to exit or to be sucked out.

Although the invention is not limited to this, the sample material is heated and/or burnt in the analyzer. According to FIG. 7a, a hollow body 53 preferable made from metal or from ceramic is provided for burning the coal content of sample material. A heating wire 54 gives out a constant heat value to the absolutely constant flow of sample material moving through the pipe 55. This process is assisted by the blower 56 with an absolutely constant rotation value, thus producing an absolutely constant transport performance. The heat emitted and the length of the heating rod 53 has been designed to ignite and burn all coal particles contained in the sample. The air-dust ratio is therefore adjusted that, on one hand, the amount of oxygen required for burning is available, but that otherwise the dust content in the stream is held as low as possible to exclude any danger of explosion during the burning process. A sensor, perhaps a thermometer 57 is fitted at sufficiently great distance from the heating rod 53. The temperature recorded by this thermometer represents a value for the coal dust content burnt at an exactly dosed amount of heat per time unit and thus—if correctly set up—a value for the combination of coal and rock fragments in the sample. The values registered with the thermometer 57 are transferred in analog or digital mode to the measurement of value processor 28. The thermometer 57 can also be replaced by one or several gas detectors or gas tracing devices or sensors. This configuration subject to the invention is very effective, since it is not necessary to heat the coal/rock dust combination to burning point, but only to the point where the coal particles begin to carbonize and to emit gases. The gases are then captured by the gas sensors, which generate a measuring impulse registering that gas is present or that it is present in a specific volume; this impulse is transferred to the converter. Coal quality varies from lode to lode, and even the amount of fugitive components vary greatly from lode to lode. For that reason, the measuring units are calibrated at the start of the winning procedure, so that the measuring procedure is programmed accordingly.

Figure 7A:
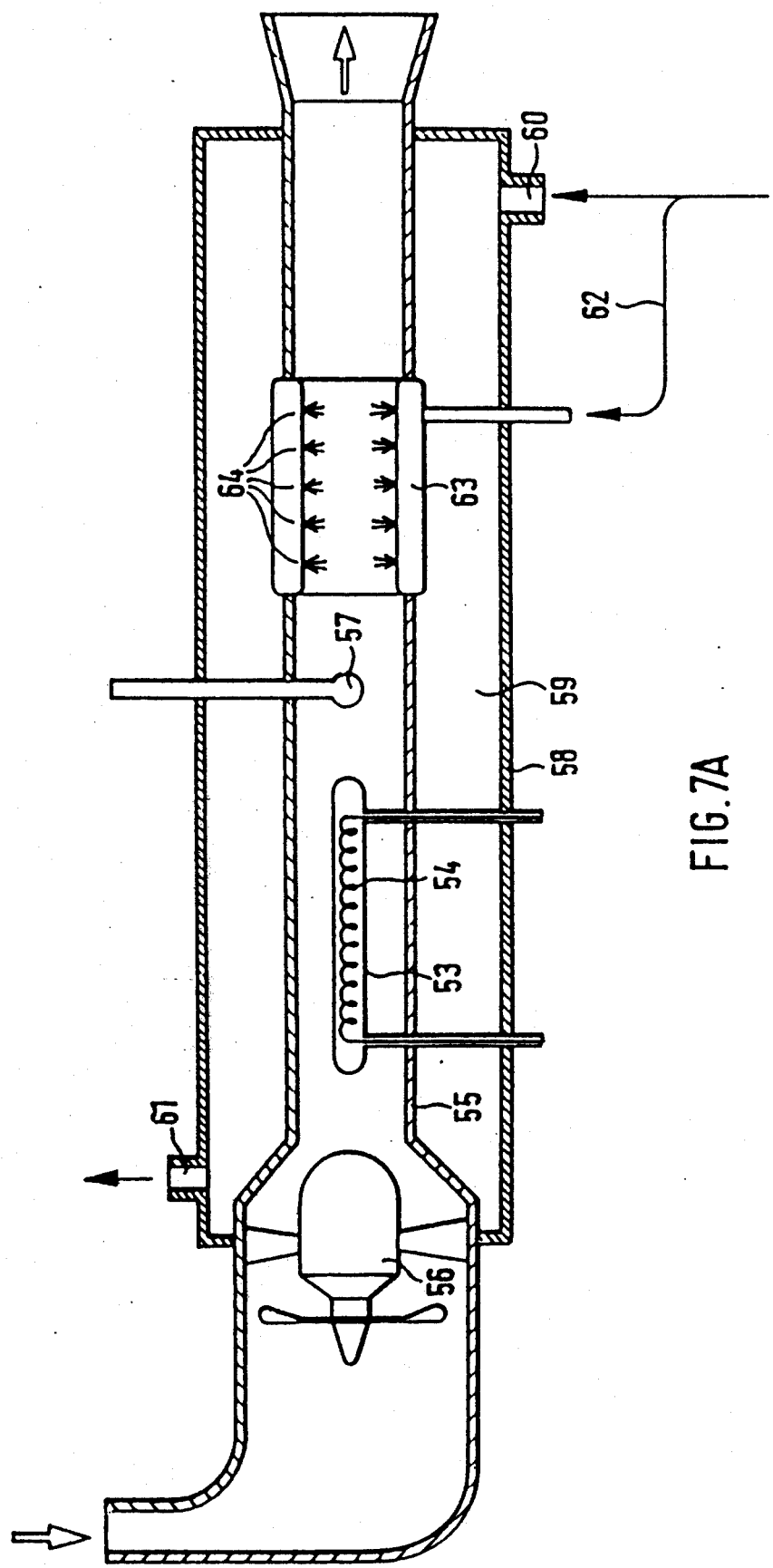
FIG. 7a is a cross-sectional view of one embodiment of a sample analyzer according to the present invention.

To ensure that an explosion is safely excluded, the metering unit is configured in accordance with FIG. 7a; this means that it is connected not only to a single or double branch connection (FIG. 2b) to ensure that only minuscule parts of the total stream flow across the heating rod 53, but it is also connected to a water container 58, which has a watercooling jacket 59 which creates an additional safety factor. The cooling container 58 should have a cool water stream flowing through, preferably in counterflow, with an inlet at position 60 and an outlet at position 61. In preference, the cooling water stream should be derived from the cooling water used for the reaming or advance machine drive motor.

A part stream 62 is branched off from the main flow immediately in front of the cooler 58, and fed into a spray unit 63. This circular spray unit has a number of jets 64 in the cylindrical interior surface, which have the function of cooling the stream of discharged gas in cases where the coal content is high to less dangerous temperatures, and douse sparks which may occur. the spray unit 63 is already a part of the waste disposal unit 27.

Figure 7B:
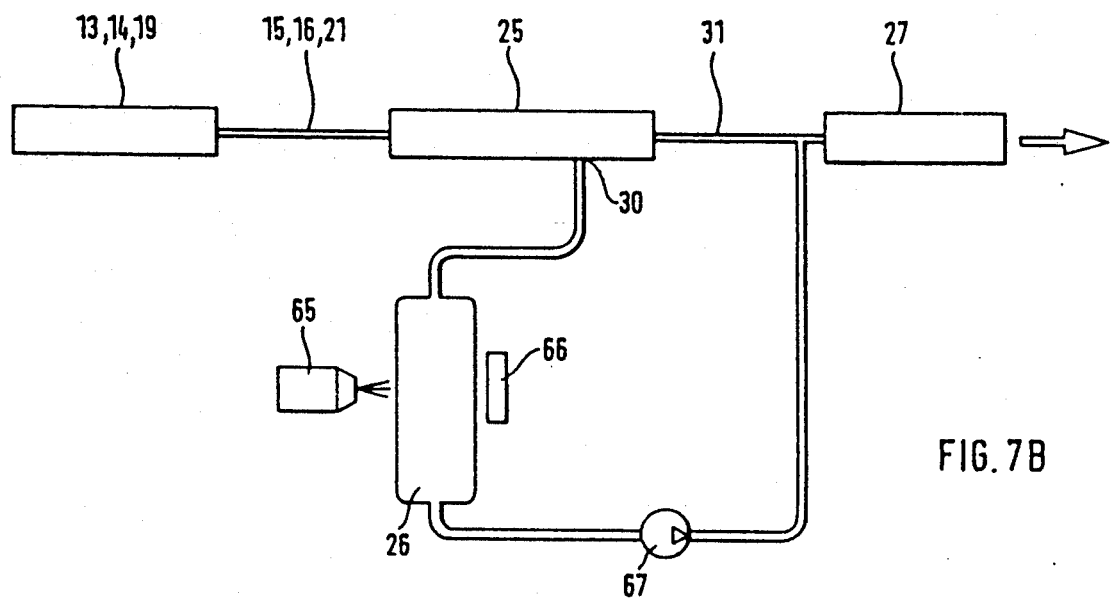
FIG. 7b is a schematic diagram of a second embodiment of a sample analyzer according to the present invention.
Figure 8A:
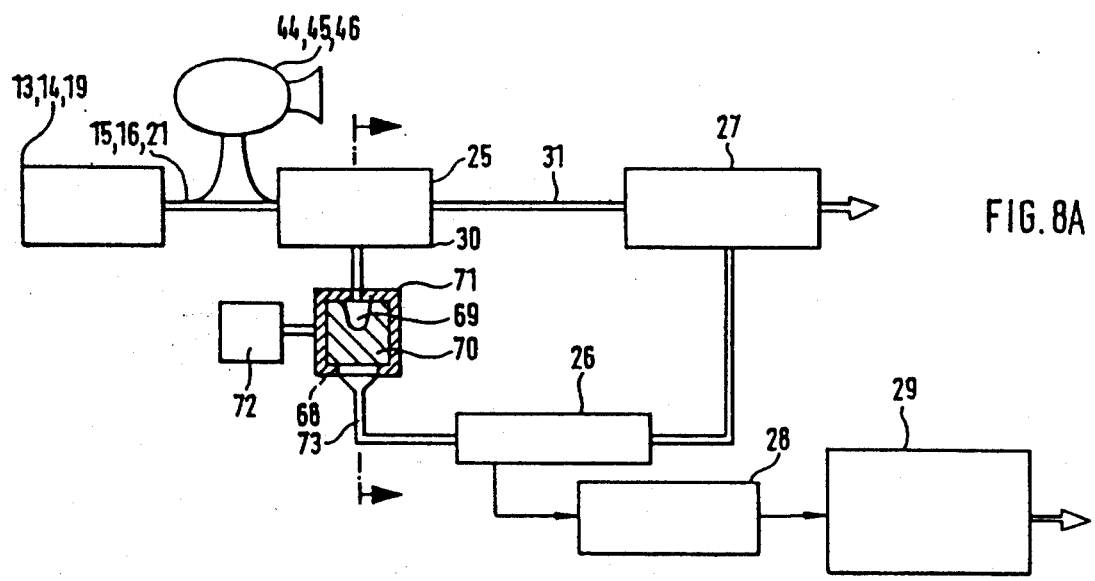
FIG. 8a is a schematic diagram of a discontinuous sampling and analyzing process according to the present invention.

FIG. 7b shows a physical analysis procedure based on a different principle. This is, according to the invention, specifically suitable for hydraulic sample transfer. As before, the analysis unit is preferable sited in the branch connection, whereby the partial stream to be fed into the measuring device is taken from position 30 at the end of the sample preparation unit 25. The analyzer 26 itself comprises a clear measuring cylinder, preferably rectangular or square in cross section, with a source of light or radiation 65 on one side, and a suitable sensor 66 on the other side. To keep the speed of flow through the measuring cylinder constant, it is recommended to install a pump 67 with a constant performance into the cycle. After the measurements have been taken, the branched-off partial stream is fed back into the main stream 31, then fed into the discharge unit 27.

Radiation of the full stream comprising coal, rock, or a coal-rock mixture opens up a number of options for measuring. The source of radiation 65 can, for instance, send out X-rays, and the sensor 66 measures the diverse reactions of coal and rock to the radiation procedure. Suitable measuring parameters in this case are luminescence and fluorescence. It is also possible to have a radiation source 65 which sends laser or infrared rays. In this case also, the diverse reactions from the coal and rock to this form of radiation is passed through the sensor 66. The radiation source 65 and the sensor 66 can be placed on opposite sides, or offset in the direction of the main stream, depending on the type of radiation used, and corresponding reactions registered from coal or rock samples.

Should discontinuous measurement procedures be employed during constant sampling, due to the fact that the physical or chemical measurement principles selected make this necessary, a discontinuous dosing unit 68 can intersect the sample preparation unit 25 and the analyser 26 see FIGS. 8a–8d. This unit comprises a rotating body 70 and dosing chambers 69, contained in a housing 71, rotating in discontinuous mode. A step-by-step selector 72 strictly controls the rotating movements of the rotating body 70 by 180 degrees per step. The conversion steps are adapted to the processing speed of the measuring unit 26. In this procedure, the chamber 69 filled by the dosing opening 30 is emptied into line 73, which feeds the discontinuous sample portions to the measuring unit 26.

The same working principle can, if a longer rotating body 71 and dosing chambers 69a, 69b, 69c and 69d offset by 90 degrees are implemented, serve to test samples from several sampling units 13, 14, 19 fed through separate pipelines 30a, 30b, 30c, 30d in the same measuring unit 26. In this case, the rotating body 70 is transferred by the step-by-step motor 72 by 90 degrees at a time. This causes the samples to be transferred by the connection line 73 to the measuring unit 26. A control system not shown then ensures that the step-by-step motor is only shifted when the previous measuring procedure has been finalized in the unit 26. This equipment also guarantees that the through-flow speed of discontinuously transferred samples is harmonized with the main volume stream 31.

FIG. 9 shows a sampling unit 13, 14, 19; this unit is fitted with a cutting device 74, which can either be a saw blade or a cutting disk. The cutting unit is fitted into fins 36 in the sampling unit housing in such a way as to permit finely ground minerals to fall through the ribs into the gap, then enter the transport units 15, 16, 21. The sealing sleeves 23, cut delimiter 37 and the other items in the configuration are similar to the sampling units in accordance with FIGS. 3a, 3b and 4. Jets 75, 76 are sited in the direction of rotation in front of or behind the cutting disk 74. When hydraulically transporting material, water is ejected, air is ejected during pneumatic transport. The cutting disk is cooled by water and air. Using the cutting method has the advantage of producing finely corned sample material, which does not require subsequent crushing before entering the measuring unit.

When sampling with the aid of the cutting disk 74, a vast quantity of fine dust is created. To assist with the prevention of silicosis, find dust measurement instruments are provided for testing coal and rock dust. These can be used as analyzers in the unit subject to this invention. This enables the user to differentiate between coal and rock dust by analyzing the fine dust content, and can make is possible to remove the crushing equipment and mixing units in the preparation process.

Figure 10:
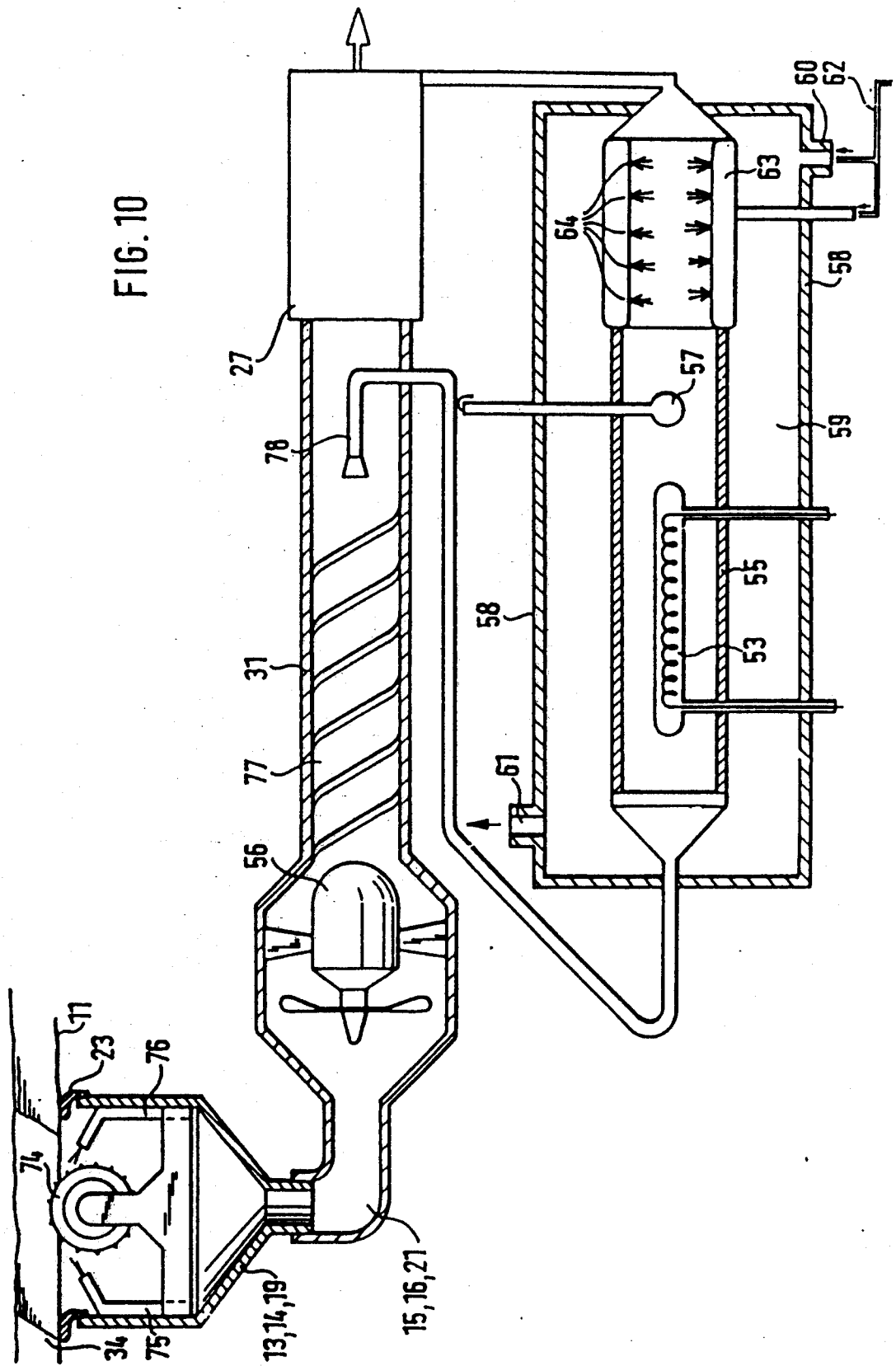
FIG. 10 is a schematic drawing of a preferred embodiment of sample-taking, transport, and analysis according to the present invention.

The most favourable combination subject to this invention is shown in FIG. 10. When the cutting disk 74 spins very rapidly, the sample material loosened in the cut is so finely corned that it is not necessary to subsequently crush it in accordance with FIGS. 7a and 7b. Compressed air is introduced over the two jets 75 and 76; this has the double function of cooling the cutting disk, and also to generate the pressure required to transport the loose sample material through the transport unit 15, 16, 21.

A blower 56 supports the transport. The mixture of air and solid material streams through the line system 15, 16, 21 and 31 at a speed which ensures that a thorough mix can be guaranteed in the guide blade system 77. The measuring procedure according to FIG. 7a requires a small amount of sample material. To remove this small quantity of material from the transported stream requires that a pressure tube 78 is installed in the connection line 31, which leads to the actual measuring unit, whose configuration is basically the same as that shown in FIG. 7a.

Figure 11:
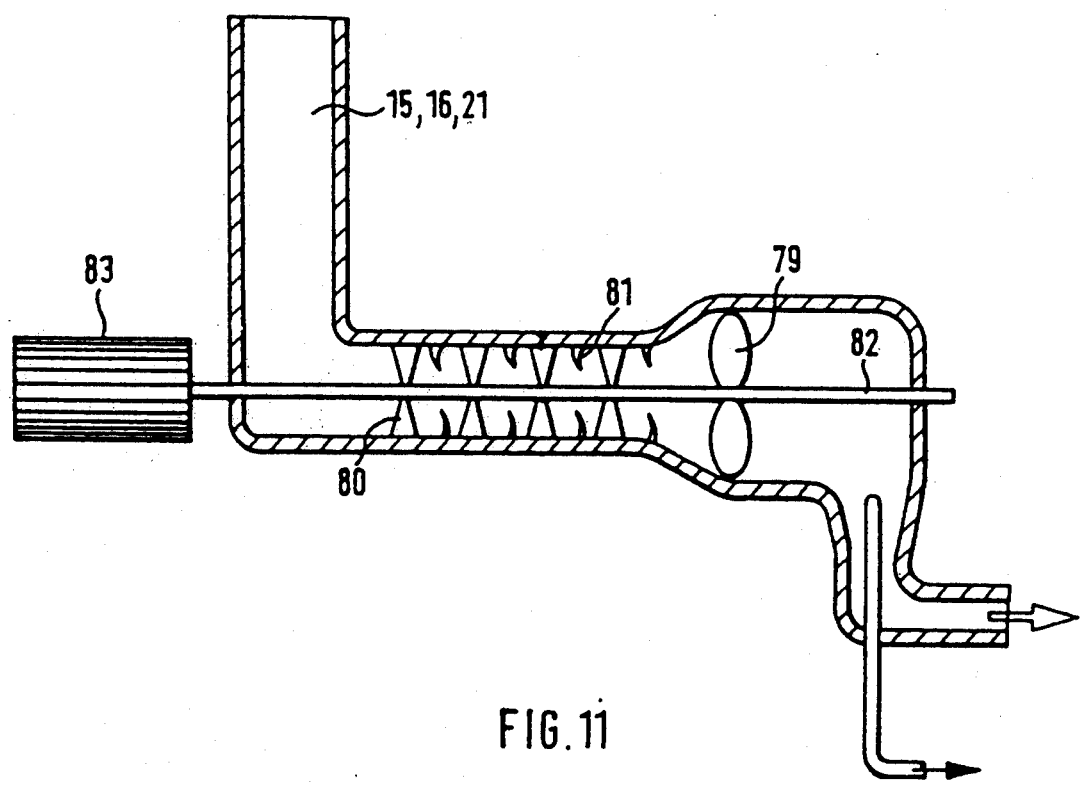
FIG. 11 is a cross-sectional view of a combination sample blower, sample crusher, and sample mixer unit according to the present invention.

FIG. 11 shows another combination comprising blower, crusher and mixer, which is compact in layout. The main stream 15, 16, 21 sucked through the blower 79 runs through a series of fly cutters 80 and guide blades 81, which are sited with the blower 79 on the same shaft 82, and are driven by a motor 83. Crushing, mixing and generating the underpressure are thus a common process.

I claim:

1. A process for controlling reaming and advance machines along a cutting horizon between coal and rock, based on a cutting tool configuration affixed to a machine, fitted with a sensor able to differentiate between coal and rock areas, whose measuring values are transformed into actuating impulses, which guide the cutting tools to the cutting horizon, comprising: taking mineral samples from behind the cutting tool at one of a perpetual rate or short intervals; analyzing the mineral samples in the sensor; comparing the analysis to a standard value; and using deviations from the standard value as measured values for the actuating impulses.

2. The process defined in claim 1, wherein the mineral samples taken are mixed and crushed prior to being analyzed.

3. The process defined in claim 2, wherein waste material from the mineral samples and the mineral sample material tested are disposed of in one of a continuous mode or in short intervals.

4. The process defined in claim 3, wherein the step of taking mineral samples includes taking a series of samples across the entire working width of the cutting tool, and the step of analyzing the mineral samples includes one or analyzing each of the series of samples singly or analyzing the series of samples in combination.

5. The process defined in claim 4, wherein crushed mineral taken from cuts into the cutting horizon is used as sample material.

6. The process defined in claim 5, wherein the sample is heated, and the coal content is defined by one of heat measurement or gas analysis.

7. The process defined in claim 5, wherein the step of analyzing the mineral samples includes photometric analysis.

8. The process defined in claim 7, further including the step of ascertaining the standard value by a learning method, and then programming the standard value.

9. The process defined in claim 8, further including the step of setting the standard value based on an analyzed value for rock, and using this value to set the cutting tool unit into the coal in time intervals, whereupon automatic control is resumed.

10. The process defined in claim 9, wherein the machine is provided with a sampling feature comprising at least one sampling tool configured behind the cutting tool configuration, a transporting unit to move crushed mineral from the sampling feature into at least one analyzer, the analyzer ascertaining the rock and coal content of the crushed mineral and producing measured values, a processor for comparing the measured values with standard values and for ascertaining the actuating impulses from differences between the measured values and the standard values, and a waste disposal unit for analysis material.

11. The process defined in claim 5, wherein the sampling tool is fitted into a housing and provided with a sealing sleeve aligned on the cutting horizon, with an abrasive surface facing the cutting horizon.

12. The process defined in claim 11, wherein the housing is affixed to a steering drive and is movable to the cutting horizon.

13. The process defined in claim 12, wherein the sampling tool comprises at least one flat chisel, the chisel being oriented so that loosened mineral is captured by one of the housing or at least one hollow chisel sited in a hollow chisel holder, whereby material cut by the flat chisels falls through passages in both the hollow chisels and in the chisel holder.

14. The process defined in claim 12, wherein the sampling tool includes at least one of a cutting disk or a saw.

15. The process defined in claim 12, further including the step of cleaning a sampling area prior to the taking of a mineral sample from the area.

16. The process defined in claim 12, wherein high pressure water power is used in taking mineral samples.

17. The process defined in claim 16, further including transporting mineral samples by one of a pneumatic conduit operatively connected with a blower or a hydraulic conduit operatively connected with a pump.

18. The process defined in claim 17, wherein the mineral samples are transported pneumatically, a sample for testing is collected on a filter cloth, and the collected test sample is removed from the filter cloth by a cleaning unit.

19. The process defined in claim 18, further including crushing and, mixing the sample material to provide prepared sample material and selecting a portion of the prepared sample mineral for analysis.

20. The process defined in claim 19, wherein the analysis operates in accordance with the low temperature carbonizisation gas method with an electrical heating rod and one of a thermometer or a gas detector sited at a set distance from this heating rod.

21. The process defined in claim 17, wherein the step of analyzing includes photometric testing of hydraulically transported samples.

22. The process defined in claim 21, wherein samples taken from several transport lines are fed in sequence across a dosing part into an analyzer.

23. The process defined in claim 1, wherein the mineral samples are transported in a stream to the sensor, the sensor including a circular spray unit affixed in the direction of the stream behind an electrical heating rod and a thermometer, the spray unit having jets sited at a cylindrical surface to cool and to remove any sparks.

24. The process defined in claim 23, wherein cooling water is taken from motors driving the reaming and advance machines.

25. The process defined in claim 24, wherein a step-by-step selector preceeding an analyzer has pockets which act as dosing units for discontinuous analysis of sample material transported to the analyzer.

26. The process defined in claim 25, further including dividing mineral samples by means of a pressure tube sited in a transport unit.

* * * * *